United States Patent [19]

Lee et al.

[11] Patent Number: 5,019,056
[45] Date of Patent: May 28, 1991

[54] BOWEL CARE APPARATUS

[75] Inventors: Alan R. Lee, Littleton; David P. Mead, Castle Rock; Robert A. Null, Littleton; Thomas Shilling, Aurora; Ray Atchley, Golden, all of Colo.

[73] Assignee: Aegis Medical, Inc., Littleton, Colo.

[21] Appl. No.: 247,734

[22] Filed: Sep. 22, 1988

[51] Int. Cl.$^5$ .............................................. A61M 5/00
[52] U.S. Cl. .................................... 604/257; 604/276
[58] Field of Search ................... 604/48, 54, 96, 113, 604/114, 118, 131, 151, 257, 259, 264, 275, 276, 280, 95, 27–35; 128/DIG. 12, 750; 600/29; 251/5; 137/102, 844, 906

[56] References Cited

U.S. PATENT DOCUMENTS

| | | | |
|---|---|---|---|
| 3,329,147 | 7/1967 | Barron | 128/230 |
| 3,485,472 | 12/1969 | Bozich | 241/5 |
| 3,570,488 | 3/1971 | Diskin | 128/230 |
| 3,771,522 | 11/1973 | Waysilk et al. | 128/227 |
| 4,190,059 | 2/1980 | Holt | 128/750 |
| 4,626,239 | 12/1986 | Ardizzone | 604/31 |
| 4,682,979 | 7/1987 | Girouard | 604/48 |

*Primary Examiner*—C. Fred Rosenbaum
*Assistant Examiner*—William Lewis
*Attorney, Agent, or Firm*—John E. Reilly

[57] ABSTRACT

A bowel care system is made up of a wheeled cart unit so as to be readily transportable between a patient and bathroom for removal of waste matter from the patient by means of colonic lavage apparatus mounted on the unit, the apparatus including a fill container and waste reservoir with a fill line extending from the fill container into communication with a speculum which is insertable into the anal canal of the patient, a pump for pumping water under pressure through the speculum, a drain line also communicating with the speculum at a location downstream of the fill line with a valve between the speculum and drain line which is movable between open and closed positions in response to differential pressure between the pump and speculum, and a timer is provided for sequentially activating and deactivating the pump over predetermined time intervals so that water is supplied under pressure over a first predetermined time interval through the speculum followed by remobal of the water and waste matter via the drain line over a second predetermined time interval.

13 Claims, 5 Drawing Sheets

BOWEL CARE APPARATUS

This invention relates to bowel care systems; and more particularly relates to a novel and improved method and apparatus for lavaging the colon.

BACKGROUND AND FIELD OF THE INVENTION

Various types of systems have been devised for irrigating and lavaging the colon for the purpose of dislodging waste or fecal material and are particularly beneficial for elderly and handicapped patients. In such systems, it is desirable that the mechanism employed be compact, sanitary and easy to use and readily conformable to meet the particular requirements and physical condition of the patient.

Typically, systems which have been employed in the past for colonic lavage have a nozzle or speculum which is inserted into the rectum and water is directed from a tank or reservoir at a predetermined temperature and pressure level through the speculum into the colon of the patient. After a predetermined time interval, the liquid and waste material are withdrawn from the patient via the speculum and through a waste or drain line into a waste container. The flow of water into the patient is regulated to some extent by closing the drain line and, once the colon is filled to a predetermined level, the drain line is opened so that the water and waste material are then free to flow back through the nozzle and drain line into the waste container. In this relation, it has been proposed to control the opening and closing of the drain line by means of a valve which is either pressure or manually operated to open and close that line either according to a particular pressure level or time interval.

Prior art systems have employed some means of attachment directly into the water supply system so that the water is delivered directly from the tap or into some form of overhead tank and then rely upon gravity feed to direct the water into the patient and, for example, reference is made to U.S. Pat. No. 3,771,522 to Waysilk et al. U.S. Pat. No. 3,750,668 to T. Perl utilizes a wheeled cart containing a liquid supply receptacle with the necessary accessory equipment for administration of enemas to groups of patients, and the supply receptacle along with a separate waste receptacle are arranged on separate shelves of the cart; however, the apparatus is not designed or capable of use for colonic lavages.

U.S. Pat. No. 2,420,507 to H. C. Stratton discloses a therapeutic irrigating system in which a pump is used to control the delivery of water or other liquid to the patient via a supply tube while clamping off a discharge line, followed by unclamping the line to permit the colon to empty into a discharge or waste container and which steps are done manually with the aid of an attendant. In U.S. Pat. No. 3,142,298 to W. L. Koski et al, the sequence of filling and discharging is automatically controlled in a stomach pump unit and provides adjustable time control means to regulate the duration of filling and evacuation but requires separate pumping mechanisms and tubes for the injection of water and evacuation of liquid from the stomach. Lacking in such systems and others is the ability to minimize the amount of water required in conducting a complete lavaging operation or sequence as well as reducing the amount of accessories and instrumentation required to conduct such operations; also, to provide a fully portable and automatic system which can be patient-operated with minimal assistance required on the part of an attendant or nurse and can be easily transported into position for use followed by removal to a bathroom area for convenient and sanitary removal of the waste matter. In this relation, it is desirable that no manual lifting is required and that the entire operation may be performed automatically in an efficient and highly dependable manner.

SUMMARY OF THE INVENTION

Accordingly, it is an object of the present invention to provide for a novel and improved bowel care system which employs a minimum number of parts, is highly efficient and dependable in use while conserving on the amount of water required to perform a complete colonic lavaging operation.

It is another object of the present invention to provide for a novel and improved method and apparatus for colonic lavage in which closely coordinated fill and drain sequences may be performed automatically or under the control of the patient in alternating cycles of operation and in a closely coordinated sequence of steps in which the duration of filling and draining may be regulated to assure maximum effectiveness and relief to the patient.

It is a further object of the present invention to provide in a colonic lavage apparatus for a novel and improved control valve which will cooperate to regulate filling and draining in response to the pressure differential of the liquid between a fluid supply and the patient.

A still further object of the present invention is to provide for a novel and improved colonic lavage apparatus which is self-contained, portable and sanitary; and further wherein a novel and improved waste removal system is provided as a part of a wheeled unit which can be transported easily between the patient and bathroom, and a waste container on the unit can be mechanically lifted and tilted for removal of waste material into another receptacle, such as, a toilet.

In accordance with the present invention, a portable apparatus for colonic lavage comprises a wheeled unit having spaced upright support members for a water fill receptacle and a waste receptacle, a fill line extending from the water fill receptacle and a speculum for insertion into the rectum of a patient for lavaging the colon, there being a drain also extending from the speculum for removal of waste matter from the colon. Lift means associated with the support members are provided for mechanically lifting and lowering the waste receptacle to facilitate removal of waste matter from the waste receptacle in a raised position. In lavaging the colon, pump means are provided for pumping water from the fill receptacle under pressure through the fill line and speculum into the colon, there being valve means in the drain line movable to a closed position when water pressure in the pump means exceeds the water pressure in the speculum and to an open position when the water pressure in the speculum exceeds that in the pump means. Timer means are provided for sequentially activating and deactivating the pump means over predetermined time intervals whereby water is supplied under pressure to said colon over a first predetermined time interval during which the valve means is closed and when said pump means is deactivated the valve means is opened by virtue of the change in pressure differential to effect removal of the water and waste matter from the colon via the drain line over a second predetermined time interval.

DETAILED DESCRIPTION OF THE PREFERRED EMBODIMENT

Figures 1, 2:
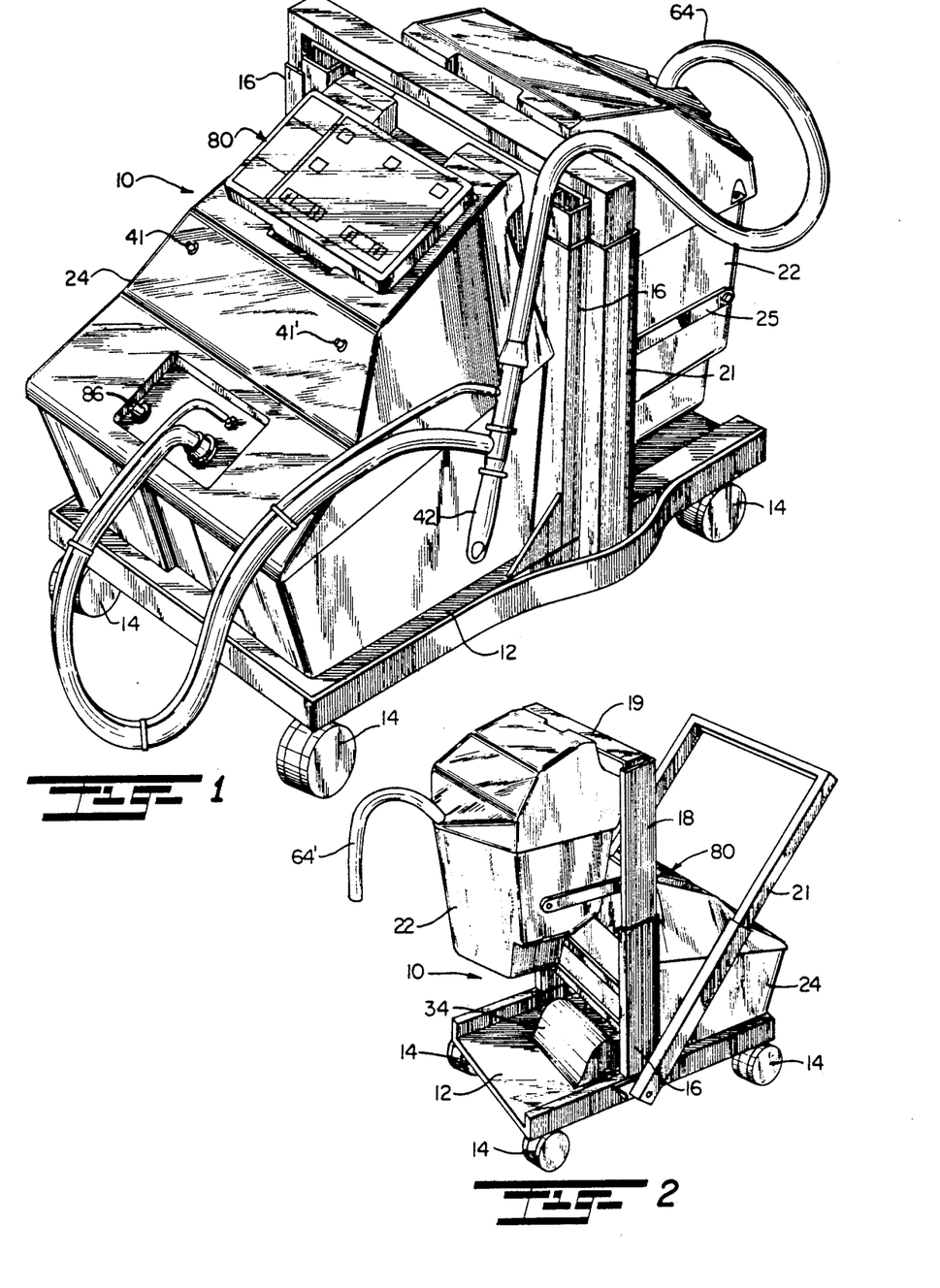
FIG. 1 is a perspective view of a preferred form of bowel care system in accordance with the present invention.
FIG. 2 is a perspective view of the preferred form of bowel care system with the waste container in a raised upright position.
Figure 3:
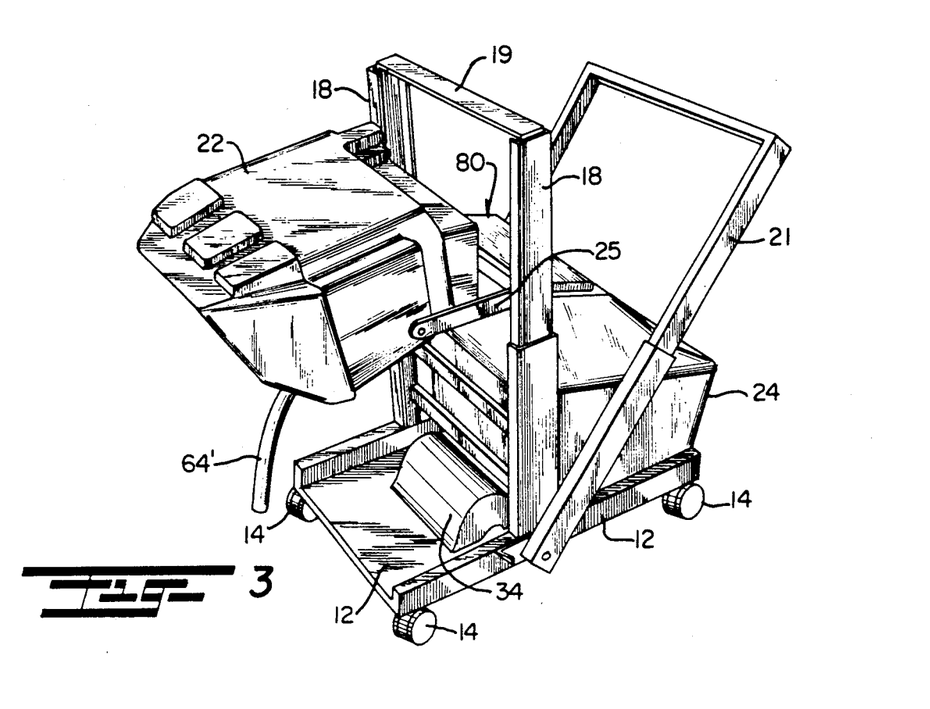
FIG. 3 is another perspective view of a preferred form of present invention with the waste container in a raised, tilted position for removal of waste matter from the container.

A preferred form of bowel care system 10 is illustrated in FIGS. 1 to 3 which is comprised of a wheeled cart unit including base 12 disposed on castors 14 and a pair of upstanding posts or supports 16 are disposed intermediately of the base 12 and on opposite sides thereof. The supports 16 are of generally channel-shaped configuration to receive slidable telescoping shields 18, and the supports 16 are disposed in facing relation to one another for receiving a lift mechanism 20 for a waste reservoir or container 22. A supply container or reservoir 24 is mounted at one end of the base 12 on the opposite side of the supports 16 to that of the waste container 22 and rests within a shallow depression formed in the base 12. A telescoping handle 21 angles upwardly from the base 12 at a convenient height to permit movement of the unit by an operator.

The waste container 22 is suspended from the lift mechanism 20 by means of horizontally extending brackets 25 which extend forwardly from vertical track members or sliders 26 telescopingly received in each of the supports 16. Each bracket 25 terminates in a pivot 28 which is attached to an upper sidewall on opposite sides of the waste container 22 in order to permit manual tipping or tilting of the waste container when lifted, as shown in FIG. 3. Each of the sliders 26 is mounted in a support 16 and a crossbar 19 interconnects upper ends of the sliders 26.

Figure 6:
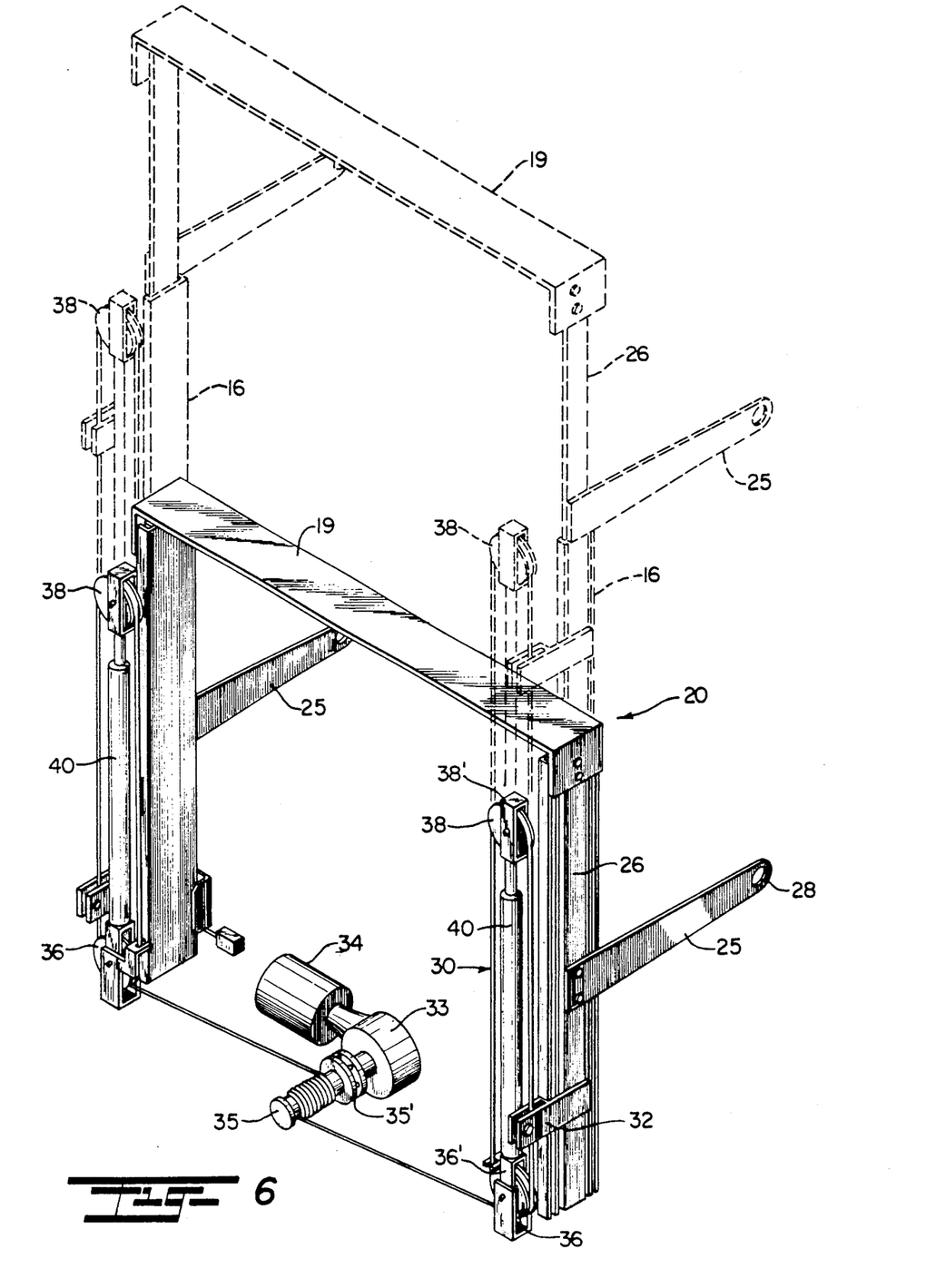
FIG. 6 is a perspective view with portions removed of a preferred form of lift mechanism for the present invention.

In order to mechanically lift the waste container 22, a cable drive 30 is arranged for extension along each slider 26. A common rotatable drive unit for synchronously operating the cable drive 30 is made up of motor 34 mounted on the base 12 including a speed reducer 33 into a common drive pulley 35, and a slip clutch 35' on the common drive pulley 35 is mounted on the drive shaft of the motor 34. The cable 30 is wrapped a number of times around the pulley 35 and extends in opposite directions for advancement around a lower guide roller 36 journaled at the lower end of each support 16 and is attached to bracket 52 which in turn extends from each slider 26. The cable 30 is directed upwardly alongside each channel-shaped support 16 and trained around an upper guide roller 38 journaled at the upper end of each support 16, then is directed downwardly and anchored at a free end to a bracket 36' at the lower end of each support 16. In the preferred form, the lift mechanism is designed as a "power-down" mechanism in which the motor drive when activated will cause the cable 30 to advance the brackets 32 and attached sliders 26 in a downward direction against the urging of gas springs 40. Each gas spring 40 is extended between a stationary bracket 36' for each lower guide roller 36 and a movable bracket 38' for each upper guide roller 38. In this way, as the motor 34 is rotated to wrap the cable around the pulley 35, the upper roller 38 will be moved downwardly against the urging of the gas spring 40 so as to multiply the travel or distance of movement of the sliders 26 in a downward direction. Conversely, when the motor 34 is reversed, it will unwrap or remove the tension from the cable so that each of the gas springs 40 will force the sliders 26 and brackets 38' upwardly to a fully extended position, as shown in FIG. 6. One suitable form of gas spring that may be employed is the Model 16-2-247-200-AM6-BM6, manufactured and sold by Suspa, Inc. of Grand Rapids, Mich. Further, for the purpose of illustration but not limitation, the motor 34 may be a Model VW3 high torque universal gear motor manufactured and sold by von Weise Gear Company of St. Clair, Miss., and the slip clutch 35' may be a "POLY-CLUTCH" manufactured and sold by Custom Products Corporation of North Haven, Conn. A "lift" control button 41 and "lower" control button 42 are provided on the container 24 and are electrically connected to motor 34 to control the lift mechanism.

Figure 5:
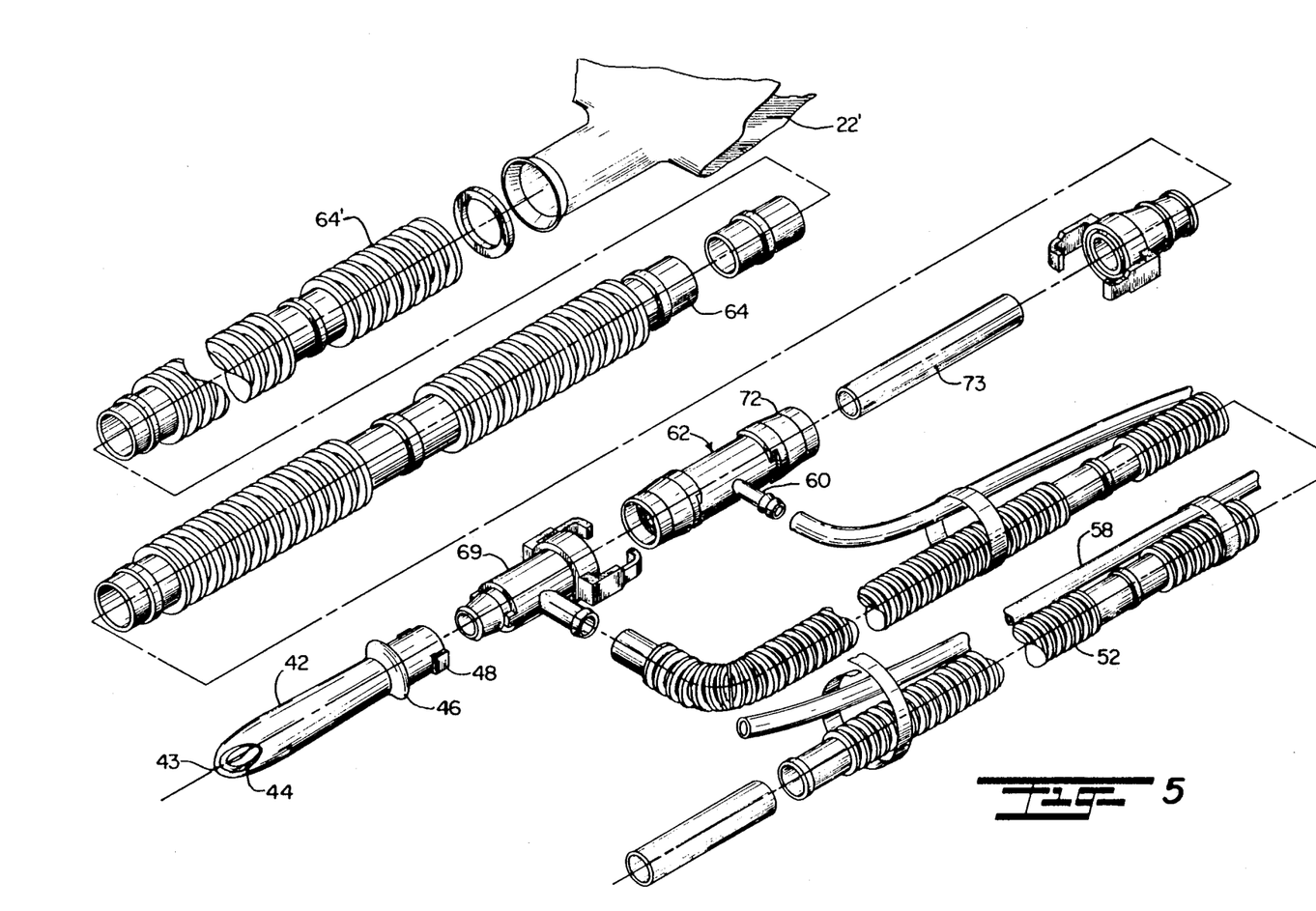
FIG. 5 is an exploded somewhat perspective view illustrating a preferred form of colonic lavage apparatus employed in the sYstem of the present invention.

As a preliminary to describing the pump circuit, reference is made to FIG. 5 and in particular to the construction and arrangement of speculum 42 which is set forth and described in more detail in copending application Ser. No. 247,736, entitled "SPECULUM FOR COLONIC LAVAGE", filed concurrently herewith and assigned to the assignee of this application. For purposes of the present invention, the speculum 42 is adapted for insertion into the anal canal of a patient and comprises a tapered end portion 43 provided with diametrically opposed eyelets 44 and an elongated tubular body 45 which tapers rearwardly from the forward tip and terminates in a connecting end portion 48 which is adapted for coupling to a control valve 62. An anal ring 46 serves as a stop adjacent to the connecting end 48 of the speculum to limit the advancement of the speculum through the anal canal and into the rectum.

An important feature of the present invention resides in the colonic lavage apparatus and which broadly consists of a pump circuit 50 mounted within the interior of the receptacle 24, the circuit including a supply tube 52 extending from the outlet of the pump 54 for connection to the speculum 42. In addition, a small diameter valve control tube 58 extends from the tube 52 at the outlet side of the pump into a pressure port 60 in a sidewall of a control or sphincter valve 62 which is connected in close proximity to the speculum, and a drain line 64 extends into the waste reservoir 22. It will be noted that the pump circuit includes two check valves 65, 65' in series to prevent return or backflow of fluid from the speculum 42; and a pair of pressure relief valves 66, 66' are connected into fill line 52 ahead of the check valves, the pressure relief valves 66, 66' being designed to open in response to liquid pressure in the water fill line 52 in excess of a predetermined level, such as, on the order of 2 psi. The pressure relief valves 66, 66' are spring-loaded valves which in a well-known manner are normally closed when the water pressure is below the predetermined level. For example, if the maximum pressure is established at 2 psi, the spring pressure is such that the valve will not open until the 2 psi level is reached and, when the water pressure exceeds that level, one of the valves will open to bypass some of the water back into the container 24. In this relation, some redundancy is built into the system so that if one of the valves 66, 66' should fail the other will be operative to open at the preset pressure level in order to avoid excess pressure in the fill line. Similarly, a pair of check valves 65 and 65' are provided so that in the event that one should fail the other is operative to prevent backflow of water through the fill line 52.

Figure 8:
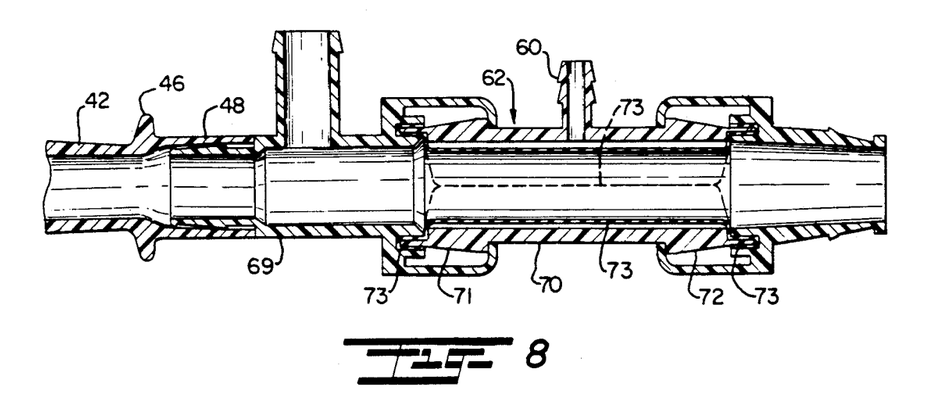
FIG. 8 is a sectional view of the speculum and valve employed in the preferred form of colonic lavage apparatus of the present invention.

The valve control tube 58 is a relatively small diameter tube in relation to the supply line 52 and supplies a small quantity of fluid under pressure from the outlet side of the pump 54 into the valve pressure port 60. As set forth and described in more detail the hereinbefore referred to copending application for patent Ser. No. 247,736, and as shown in more detail in FIG. 8, the valve 62 comprises an outer inflexible housing or body 70 having a barbed end portion 71 coupled by pressfit insertion to one end of a T-shaped fitting 69 which forms an axial continuation of the speculum 42. An opposite end portion 72 is coupled to a fitting 68 at one end of the drain line 64 so that the speculum 42, valve 62 and drain line 64 are securely connected in fixed, end-to-end relation to one another. A thin-walled elastomeric liner or sheath 73 is positioned within the housing to define a flexible valve member having an outer diameter corresponding in its fully dilated position to the inner diameter of the tubular housing 70. Opposite ends 73' of the liner 73 are connected by doubling each end of the liner 73 back upon itself and stretching it to fit over the external wall surface at either end of the valve body 70. In this way, an excellent seal is effected with the housing without bonding or clamping the liner at the ends and will form a sealed annular passageway or space between the outer liner surface and the inner surface of the housing 70. The pressure port 60 is located intermediately of the ends of the liner valve body 70 and receives fluid or liquid under pressure via the tube 58 for introduction into the sealed passageway. The valve 62 operates on the principle of remaining in an open position as long as the pressure inside of the control valve 62 exceeds that delivered through the pressure port 60. Conversely, the liner will close, as illustrated in dotted form in FIG. 8, when the pressure in the valve tube 58 exceeds that of the water pressure in the speculum or valve interior. Design of the valve permits the valve to be highly sensitive to differential pressures and, for example, requires a difference of less than ¼ psi between the colonic pressure and pressure in the valve tube to close.

Figure 7:
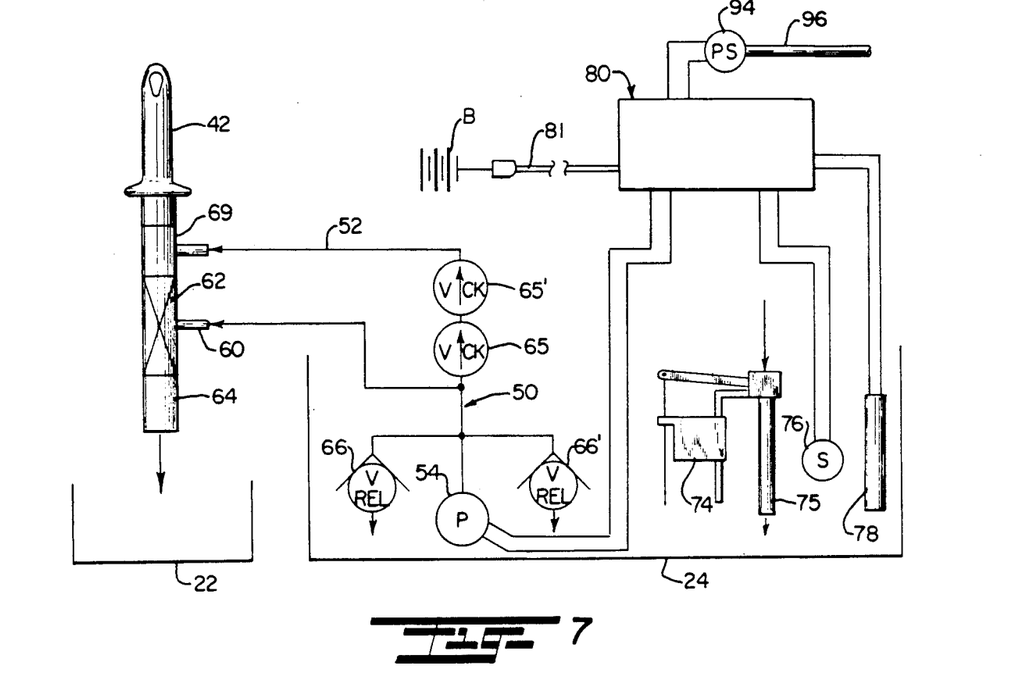
FIG. 7 is a schematic view of a pump circuit and associated sensors and controls for the lavage apparatus of the present invention.

As shown in FIG. 7, a standard float valve 74 is mounted in direct association with inlet tube 75 in the supply receptacle 24 to sense the water level in the receptacle 24 and to interrupt the flow of water supply into the receptacle when it reaches a predetermined level, for example, 5 gallons. A suitable form of float valve 74 is a Fluidmaster Model 702, manufactured and sold by Fluidmaster, Inc. of Anaheim, Calif. In addition, a float switch 76 is positioned at the lower end of the reservoir 22 and senses a low water condition in the reservoir 22 to turn off the pump 54. One commercially available switch is a Model 504 float switch, manufactured and sold by Revere Corporation of America, Wallingford, Conn. The pump 54 may be a Supersub 88 electric pump manufactured and sold by Munster Simms Engineering, Ltd. of. Bangor, Northern Ireland.

A conventional form of temperature sensor or probe as represented at 78 is provided to sense the temperature level of the water in receptacle 4, such as, a Model 8D590LH, manufactured and sold Analog Devices of Norwood, Mass.

In the preferred form of pump circuit 50, when the pump 54 is activated, water is discharged under pressure through the water fill line 52 and the speculum 42. Water is simultaneously directed under pressure from the pump via pressure tube 58 to the valve 62 and, so long as the water is flowing freely into the colon, the water pressure in the pressure tube 58 will exceed that in the speculum or colon thereby causing the valve 62 to close. If the flow into the colon should exceed the capacity of the colon, this condition will be detected by a rapid increase in pressure of the water in the fill line 52 and once the pressure reaches the maximum pressure level of the pressure relief valves, such as, 2 psi will cause one of the valves 66, 66' to open and return water into the supply receptacle.

At the end of a fill cycle, the pump 54 is deactivated to discontinue flow of water into the fill line 52, and the sphincter valve 62 will then open as a result of the greater pressure of the return flow of water from the patient via the speculum into the interior of the valve 62 and the absence of pressure in the pressure tube 58. The fluid contents of the colon are thereby allowed to be removed through the drain line 64 into the waste reservoir 22. The drain sequence will continue for a predetermined time interval necessary for removal of the liquid and waste and as aided by the peristaltic action of the patient. The fill and drain cycles are then repeated until the patient terminates the treatment or an alarm condition should turn the unit off. Specifically, the alarm conditions are (1) low water, (2) low or high water temperature, (3) low battery charge, (4) charger plugged in, or (5) lift motor plugged in.

Figure 4:
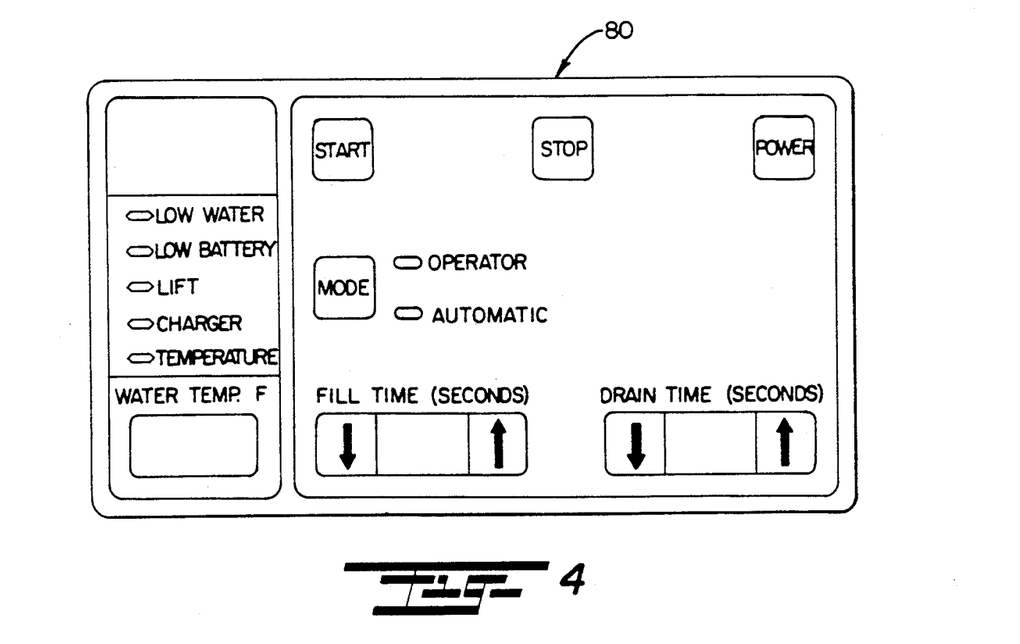
FIG. 4 is a front view in elevation of a control panel employed in association with a preferred form of invention.

Referring to FIGS. 1 and 4, there is illustrated a front panel layout of a modular panel unit 80 which is affixed by an extension cord or cable 81 to a suitable battery power source B. In this way, the patient may remove the panel unit 80 from a shelf or inset portion 84 on the exterior of the supply receptacle 24 for convenient control of the operation of the system. The preferred form of system is designed to operate on 12-volt battery power, but the lift motor 34 is designed to operate on nominal 115 volt, 60 Hz AC line power. Referring to the panel lights, if the battery is too low for the unit to properly treat a patient, the treatment mode is disabled and the low battery alarm light will be constantly illuminated. Even under low battery conditions, a bypass switch is operational to allow the supply receptacle 24 to be pumped out. Further, when the battery B is being charged, the treatment mode will be disabled but the lift motor will continue to be operational. A battery charger, not shown, is of conventional form and is designed to plug into a three-wire 115-volt AC wall outlet and, when so connected, will light the "charger" light on the panel. One suitable form of battery B is the Model NP4-12 sold by Yuasa Battery, Inc. of Santa Fe Springs, Calif. When the lift motor is powered, the "lift" light is illuminated; and when the water level is too low, the float switch 76 will cause the "low water" light to be illuminated and a relay, not shown, disconnects power from the unit. The "low battery" light requires a two-step operation: When the battery approaches a low charge such that a treatment cannot be completed, the "low battery" light will start to flash, and when the charge drops to a level such that it cannot properly power the pump, the "low battery" light will be constantly illuminated. If the water temperature is either too high or too low as sensed by the probe 78, the "temperature" light is constantly illuminated. In addition, the "mode", "start", "stop" and "power" buttons have indicator lights. When the "power" button is depressed, power is toggled on and off. When the power is on, the "power" button lights constantly and the other displays are activated. When power is off, all displays are off and no controls are active except for the "power" button which can be toggled to the power-on state.

When the "mode" button is depressed, the mode toggles between "operator-controlled" and "automatic". In the operator control mode, the light adjacent that label is illuminated, and when in the "automatic" mode, the light adjacent that label is illuminated.

"Fill Time (Seconds)" and "Drain Time (Seconds)" are selected by the operator depressing either of the arrowed up or down buttons associated with the display to increase or decrease the number of seconds indicated. Generally, the time intervals may be selected over a range of 1 second to 29 seconds, but most typically would be on the order of 6 seconds fill time and 12 seconds drain time. Once these values are selected and displayed on the panel, the lavage operation is initiated by depressing one of the "mode" buttons followed by the "start" button. If in the "operator control" mode, the system will run through one complete fill and drain cycle, then stop until the operator presses the mode button once again. In the automatic mode, the unit will continue to cycle either until terminated by the operator depressing the "stop" button or a low water condition is reached as described earlier.

In carrying out a typical operation, the fill reservoir has a fitting or port 86 for connection of a hose from a source of tap water, such as, the standard plumbing system in a building to deliver hot and cold water via the inlet tube 75 into the receptacle 24, and the temperature of the water is controlled to be in the range of 92° F. to 104° F. Otherwise, if the water in the reservoir 24 is outside the requisite temperature level, the system is not operable and the temperature light on the panel will be activated. The machine is filled to a 5-gallon level in reservoir 24, and the float valve 74 is activated when filled to that point to prevent any more water from being introduced into the reservoir.

The optimum fill/drain sequence is determined by trial and error for a given patient and specifically to determine the time duration necessary to fill the colon cavity with water. Typically, for a pump operating at a capacity on the order of 2 gallons per minute, the duration of fill may be on the order of 12 seconds at a pressure level of less than 2 psi. For most effective use, the patient is placed in a prone position and at a level above the waste reservoir 22. A speculum 42 is inserted through the anal canal and into the rectum. When a fill sequence is initiated in the manner described, the pump 54 is activated to pump water through the fill line 52. If at any time during the fill sequence or interval the pressure should increase to the maximum 2 psi level, one of the pressure relief valves 66, 66' will be caused to open so that the water is bypassed directly back into the reservoir.

At the end of the fill interval, the pump is turned off, as a result of which the pressure in the valve control line 58 is removed and the pressure or head of water and as aided by any peristaltic action of the patient is sufficient to open the liner valve 62 for the purpose of draining downwardly through the drain line 64 into the waste reservoir 22. Either one of the check valves 65, 65' will prevent return flow of the liquid and waste matter through the fill line 52. During the fill sequence, the differential pressure between the fill line 52 and valve control line 58 is on the order of ¼ psi and in this way the greater pressure in the valve control line 58 will cause the liner valve 62 to remain closed during the fill operation. Of course, any patient-induced pressure during the fill cycle which would cause the return pressure in the speculum acting against the interior of the valve liner 73 to be greater than that in the control tube 58 would cause the valve 62 to open temporarily during the fill cycle to relieve or reduce that pressure in the colon.

Removal of water and waste material during the drain sequence is aided by any peristaltic action of the patient, and the duration of that sequence will be governed greatly by the ability of the patient to assist in draining or removal of waste. Typically, the fill/drain sequence is repeated over a number of cycles and may, for example, require a total time duration of 15 to 20 minutes either until the water supply is depleted in the reservoir or the patient or attendant can see that the water is clear and no further waste material has to be removed. Here, the float switch 76 in the reservoir 24 will signal a low water condition and automatically turn off the pump 54 as well as light the display light on the panel.

At the end of a complete cycle, the waste bag 22' in the waste reservoir 22 is emptied preferably by disconnecting the end of the drain line 64 and rolling the unit 10 into the bathroom. The waste receptacle 22 is aligned with the toilet and the lift mechanism 20 activated by the electrical lift button to raise the receptacle to a level necessary to permit the waste bag 22' to be tilted. Once raised to the desired height, the waste container 22 is tilted to remove the contents in the bag 22' through a separable tube portion 64' of the drain line 64 into the toilet.

As will be seen from FIG. 5, those elements making up the colonic lavage apparatus consisting of fill line 52, control line 58, speculum 42, fitting 69, valve 62, drain line 64 and waste bag 22' are intended for one-time use. Thus, at the completion of a procedure, all that is required is to disconnect the fill line 52 and control line 58 from the container 24, and to remove the bag 22' from the waste reservoir and replace with a new assembly. Preferably, the speculum 42 and valve 62 are so fabricated with pressfit and snap locks that efforts to disassemble for cleaning or subsequent reuse will destroy them, thus avoiding exposure to infectious waste materials caused by indiscriminate reuse. In addition, the articles making up the assembly can be suitably constructed of materials having a low melting point which will self-destruct if subjected to high temperature sterilization.

It will be evident from the foregoing that the system of the present invention lends itself particularly well to patient operation and control with a minimum of assistance required on the part of a nurse or attendant. The panel 80, being connected through a separate cable 81 to a battery power source, enables the patient when in the prone position to manipulate any of the controls on the panel. Once the fill time and drain time are set for a particular patient, the patient may control starting and stopping of the system; also, if the patient is ambulatory, he will be able to wheel the unit into the bathroom for removal of the contents and replacement of the disposable assembly as described. The control valve 62 is located in close proximity to the trailing end of the speculum and directly adjacent to the connection of the fill line into the speculum so as to conserve on the amount of water pumped out of the fill receptacle 24 during each fill cycle. In this way, the amount of water stored in the fill receptacle 24 for a complete lavage procedure or operation is substantially reduced and accordingly the overall size of the receptacles 22 and 24 are substantially reduced thereby resulting in an extremely compact and lightweight but self-contained unit.

The valve 62 requires no close-fitting, movable parts that otherwise could increase the risk of sticking. The valve 62 works at a very small differential pressure on the order of ¼ psi, the minimal differential pressure needed for valve closure being established as a result of the direct connection of the pressure control line 58 from the outlet of the pump into the confined space surrounding the liner when compared to the pressure losses through the fill line 52, valves, fitting 69 and speculum 42 into the colon area.

As illustrated in FIG. 7, a sip-and-puff control switch 94 is made available as an accessory for parapalegic patients unable to manipulate the controls on the panel other than by way of grasping a tube 96 between the teeth and exhaling or inhaling to regulate the starting and stopping of the unit. The switch 94 may be a commercially available switch, such as, that manufactured and sold by MPL Company of Ft. Lauderdale, Fla., and is electrically connected to the "start" and "stop" controls. Blowing into the tube to create a positive pressure will cause the unit to be activated or started, and sucking on the tube 96 to create a negative pressure will stop the unit. Again, once the speculum is placed in position in the patient and ready for operation, it is no longer necessary for the attendant to assist in the lavage procedure itself.

It is therefore to be understood from the foregoing that various modifications and changes may be made in the construction and arrangement of elements comprising the preferred embodiment of the invention as described herein without departing from the spirit and scope of the present invention as defined by the appended claims.

We claim:

1. Colonic lavage apparatus comprising: a spectrum insertable into the rectum of a patient for lavaging the patient's colon and extracting waste matter therefrom;
   a source of liquid under pressure including fill line means communicating with said speculum for delivering liquid under pressure through said speculum into the colon;
   drain line means communicating with said speculum for drawing said liquid and extracted waste matter from the colon; and
   valve means interposed between said speculum and said drain line means including means communicating with said liquid pressure source whereby said valve means is directly responsive to the pressure of said liquid in said fill line means exceeding the pressure of said liquid in said speculum to move to a closed position in order to prevent the flow of said liquid therethrough and is directly responsive to the pressure of said liquid in said speculum exceeding the pressure of said liquid in said fill line means to move to an open position for draining said liquid and extracted waste matter from the colon of the patient.

2. Apparatus according to claim 1, said source of liquid under pressure including pump means for pumping liquid under pressure through said speculum into the colon, and timer means for sequentially activating and deactivating said pump means over predetermined time intervals whereby liquid is supplied under pressure via said fill line over a first predetermined time interval and liquid and waste matter are removed via said drain line over a second predetermined time interval.

3. Apparatus according to claim 2, said timer means being adjustable to regulate the duration of each said first and second time intervals.

4. Apparatus according to claim 1, said valve means including an outer inflexible tubular housing having one end connected to said speculum and an opposite end connected to said drain line, and an inner flexible elastomeric liner of tubular configuration and of a diameter substantially corresponding to an inner diameter of said housing, opposite ends of said line being doubled over said one end and said opposite end of said housing, and end connector means for connecting said opposite ends of said flexible inner in sealed relation to said one end and said opposite end of said housing whereby to define a sealed annular space between said liner and said housing.

5. Apparatus according to claim 4, said valve means including a port in said housing, said port in communication with an outlet end of said pump for introduction of liquid from said pump into said annular space in surrounding relation to said liner.

6. Apparatus according to claim 5, said liner having an inner diameter in the open position which is slightly greater than said speculum.

7. Apparatus according to claim 1, including a pressure relief valve means in said fill line to limit the maximum pressure level of liquid introduced into said speculum.

8. Apparatus according to claim 7, said apparatus including a fill container, and said pressure relief valve means operative to diverting liquid from said fill line into said fill container when the liquid pressure is in excess of the maximum pressure level.

9. Apparatus according to claim 1, said pumping means being battery-operated, and a control panel releasably positioned on said apparatus including said timer means for sequentially activating and deactivating said pump means over predetermined time intervals.

10. Colonic lavage apparatus comprising:
    a speculum insertable into the rectum of a patient for lavaging the patient's colon and extracting waste matter therefrom;

water fill line means communicating with said speculum for delivering water under pressure through said speculum into the colon;

pump means associated with said water fill line means for pumping water under pressure through said speculum into the colon;

drain line means communicating with said speculum for draining said water and extracted waste matter from the colon;

valve means connected in end-to-end relation between said speculum and said drain line means including means communicating with said liquid pressure source whereby said valve means is directly responsive to the pressure of said water in said fill line means exceeding the pressure of said water in said speculum to move to a closed position in order to prevent the flow of said water therethrough and is directly responsive to the pressure of said water in said speculum exceeding the pressure of said water in said fill line means to move to an open position for draining said water and extracted waste matter from the colon of the patient; and adjustable timer means for sequentially activating and deactivating said pump means over predetermined time intervals whereby water is supplied under pressure via said water fill line means over a first predetermined time interval and the water and waste matter are removed via said drain line over a second predetermined time interval.

11. Apparatus according to claim 10, said valve means including an outer inflexible tubular housing and an elastomeric liner of tubular configuration and of a diameter substantially corresponding to an inner diameter of said housing including means for connecting opposite ends of said flexible liner in sealed relation to opposite ends of said housing whereby to define a sealed space between said liner and said housing, a port in said housing, said port in communication with an outlet end of said pump means for introduction of water from said pump into said sealed space and in surrounding relation to said liner.

12. Apparatus according to claim 11, said liner having an inner diameter in the open position which is slightly greater than said speculum and collapsible into a position closing said valve means along the substantial length of said housing.

13. Apparatus according to claim 11, including pressure relief valve means associated with said water fill line to limit the maximum pressure level of water introduced into said speculum, and said pressure relief valve means bypassing water from said water fill line into a fill container when the water pressure is in excess of the maximum pressure level.

* * * * *